(12) United States Patent
Tung

(10) Patent No.: US 8,608,717 B2
(45) Date of Patent: Dec. 17, 2013

(54) URINE COLLECTION APPARATUS

(75) Inventor: Su-Lien Tung, Luzhou (TW)

(73) Assignee: Chih-Hung Lai, Taichung (TW)

( * ) Notice: Subject to any disclaimer, the term of this patent is extended or adjusted under 35 U.S.C. 154(b) by 725 days.

(21) Appl. No.: 12/759,377

(22) Filed: Apr. 13, 2010

(65) Prior Publication Data

US 2011/0251573 A1  Oct. 13, 2011

(51) Int. Cl.
*A61F 5/44* (2006.01)
(52) U.S. Cl.
USPC ............................ 604/349; 604/346; 604/347
(58) Field of Classification Search
USPC ......................................... 604/346, 347, 349
See application file for complete search history.

(56) References Cited

U.S. PATENT DOCUMENTS

| | | | | | |
|---|---|---|---|---|---|
| 4,713,067 | A | * | 12/1987 | Rothenberg et al. | 604/353 |
| 5,002,541 | A | * | 3/1991 | Conkling et al. | 604/319 |
| 5,211,642 | A | * | 5/1993 | Clendenning | 604/410 |
| 5,495,858 | A | * | 3/1996 | Steer et al. | 128/885 |
| 5,616,138 | A | * | 4/1997 | Propp | 604/317 |
| 6,551,293 | B1 | * | 4/2003 | Mitchell | 604/353 |
| 6,592,560 | B2 | * | 7/2003 | Snyder | 604/331 |
| 2002/0193763 | A1 | * | 12/2002 | Kulikov | 604/353 |
| 2010/0094173 | A1 | * | 4/2010 | Denton et al. | 600/584 |

* cited by examiner

*Primary Examiner* — Michele M Kidwell
(74) *Attorney, Agent, or Firm* — Apex Juris, pllc; Tracy M. Heims

(57) ABSTRACT

A urine collection apparatus includes a urine cover, a buffer member, and a pipe. The urine cover has an edge, a room therein, and an opening and an aperture communicated with the room, and a user's penis enters into the room via the opening. The buffer is connected to the edge of the urine cover with a connecting surface thereon to be in touch with the user's skin. The pipe is connected to the aperture of the urine cover to direct urine to a desired location.

9 Claims, 7 Drawing Sheets

URINE COLLECTION APPARATUS

BACKGROUND OF THE INVENTION

1. Field of the Invention

The present invention relates generally to a device for urinating, more particularly to a urine collection apparatus that is easy and convenient to use.

2. Description of the Related Art

In order to solve the problem of man having the urgency of going to the bathroom but can't make it in time, a urine collection apparatus to cover penis was created to meet this need for occasions like long meetings, or for those physically challenged. A conventional urine collection apparatus 1 shown in FIGS. 1 and 2 includes a trouser member 2, on which a urine cover 3 is provided corresponding to user's penis, and a pipe 5 connecting the urine cover 3 to a urine bag 4.

Even though the urine collection apparatus 1 can solve the problem of urinating difficulty or being unable to go to the bathroom in time, there are some drawbacks in its structure, for example:

1. While using the urine collection apparatus 1, the user has to put his penis at a draining outlet 3a of the urine cover 3, which is a junction of the urine cover 3 and the pipe 5, or urine may overflow or backflow and makes future cleaning more difficult.

2. Even the urine cover 3 of the urine collection apparatus 1 holds a room 3b therein, it is still difficult for the user to steadily aiming his penis at the draining outlet 3a, and the room 3b of the urine cover 3 may lead to a difficult positioning during urinating.

3. The urine bag 4 of urine collection apparatus 1 can be changed, yet the urine cover 3 is difficult to clean and maintain, which may cause hygiene problem of the urine collection apparatus.

4. In order to keep the room 3b of the urine collection apparatus 1 complete so the user feels comfortable placing the penis inside, the urine cover 3 is often made of a rigid material. Therefore, when an edge of the urine cover 3 presses the user's skin, the rubbing often causes uncomfortable feelings to users.

SUMMARY OF THE INVENTION

The primary objective of the present invention is to provide a urine collection apparatus, with the advantages of collecting urine effectively, being comfortable to use and easy to clean.

To meet the objective of the present invention, the urine collection apparatus includes a urine cover, a buffer, and a pipe. The urine cover has an annular face and a room therein, with an opening and an aperture communicated with the room. A user's penis enters into the room via the opening. The buffer is provided on the edge and has a contact surface to be in touch with the user's skin, and the pipe is connected to the aperture.

In an embodiment, the present invention provides a flexible sheet whose edge is connected to the edge of the urine cover, with an opening thereon to support the user's penis. Furthermore, the urine cover of the present invention has a ring connected to the sheet and around the opening in order to better support the use's penis.

In an embodiment, the urine cover of the present invention has a cleaning hole and a cap. The cleaning hole is connected to the room so washing detergent can be added therefrom, and the cap can be used to cover the cleaning hole.

In an embodiment, the buffer of the present invention is an air bag which can ease the user's uncomfortable feelings while being in touch with the user's skin.

In an embodiment, the pipe of the present invention is connected to the urine cover with one end, and the other end having a connecting section connected a urinating unit.

DETAILED DESCRIPTION OF THE INVENTION

Figure 1:
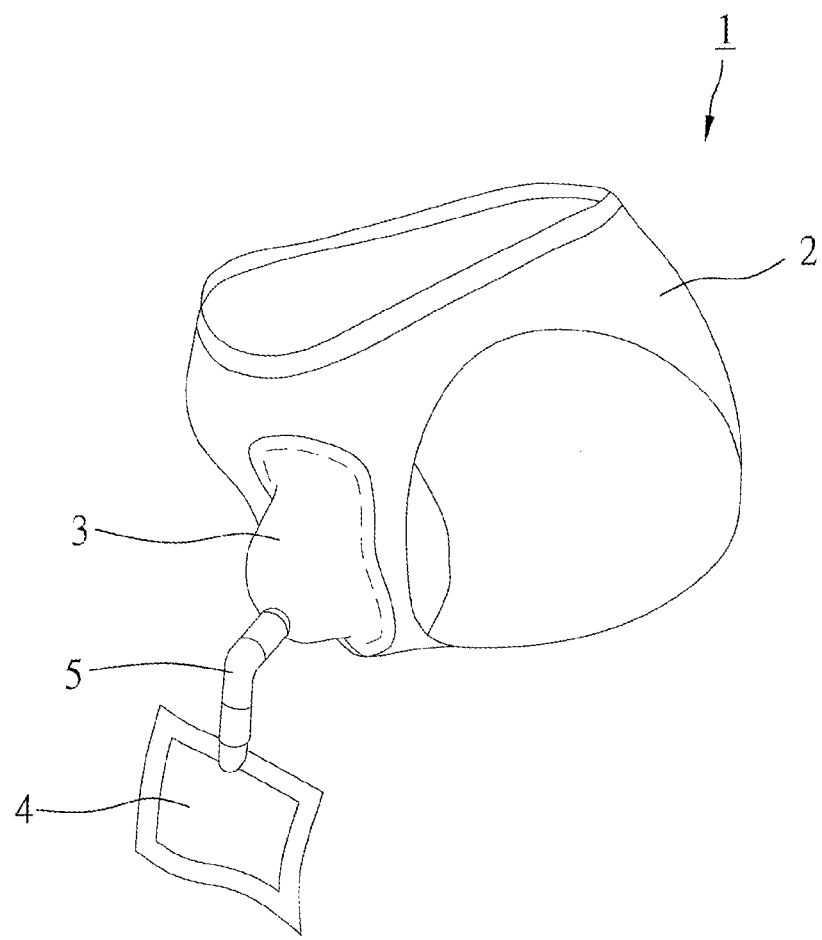
FIG. 1 is an exploded view of the conventional urine collection apparatus.
Figure 2:
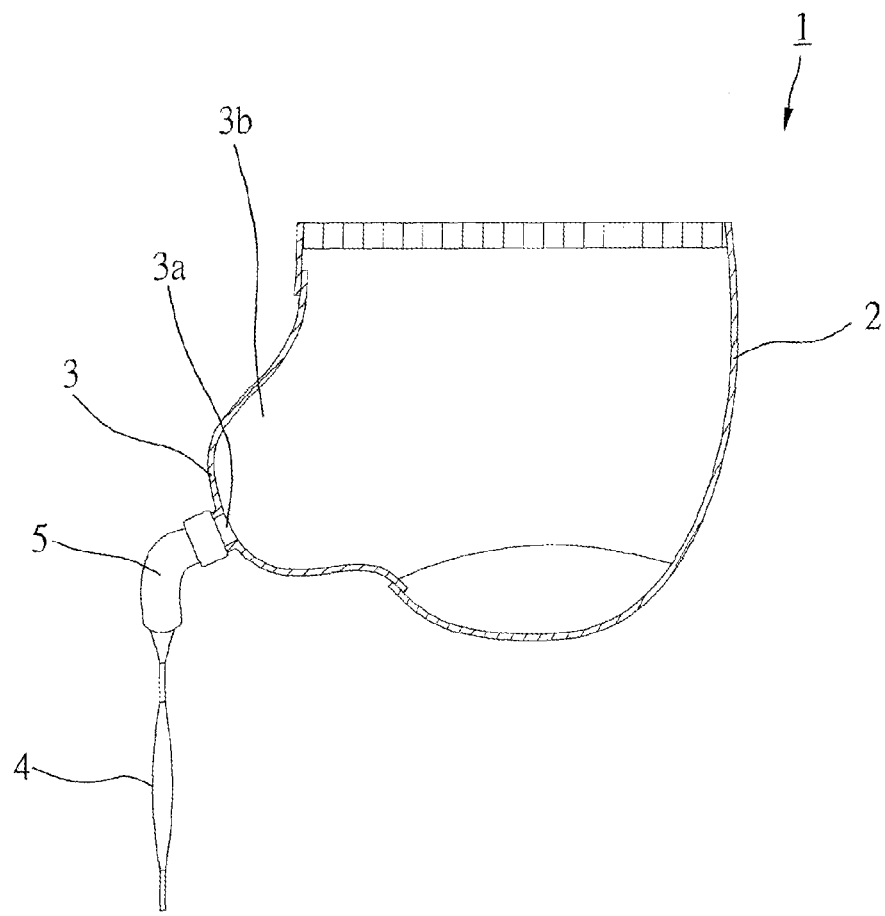
FIG. 2 is a sectional view of the conventional urine collection apparatus.
Figures 3, 4:
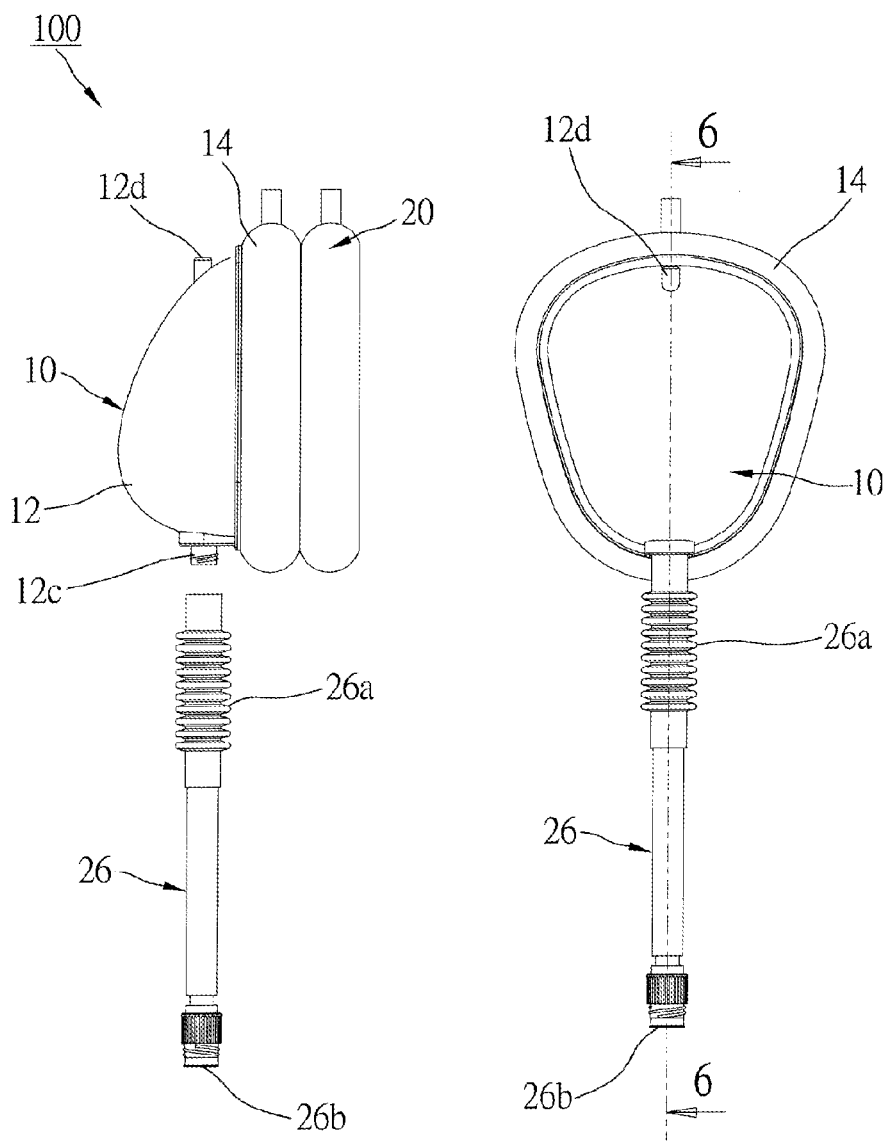
FIG. 3 is a right view of a preferred embodiment of the present invention.
FIG. 4 is a front view of t the preferred embodiment of the present invention.
Figure 5:
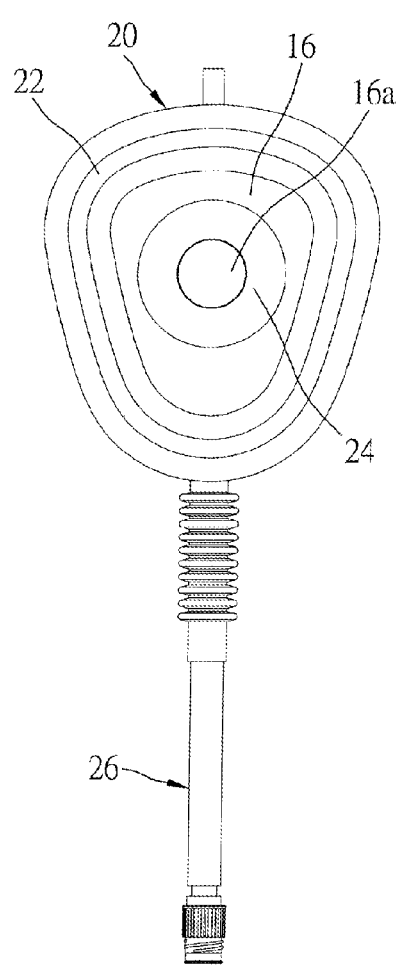
FIG. 5 is a rear view of the preferred embodiment of the present invention.

A urine collection apparatus 100 for man of the preferred embodiment of the present invention, as shown in FIGS. 3 to 6, includes a urine cover 10, a buffer 20, and a pipe 26.

The urine cover 10 is combined with an adjustable weaved cloth to be wore by a user. In the present embodiment, the urine cover 10 includes a covering member 12, an air bag 14, and a sheet 16. The covering member 12 is curved outwardly to form a room 18 therein and has an edge 12a. The air bag 14 is arranged on the entire edge 12a of the covering member 12, with an annular face 14a on an outer side. The sheet 16 has good flexibility, with its edge connected to the annular face 14a of the air bag 14, with an opening 16a at a center thereof communicated with the room 18. The buffer 20 is an annular air bag in the present embodiment, and is fixed to the annular face 14a of the air bag 14. An outer side of the buffer 20 has a contact surface 22, which is in touch with the user's skin to provide a comfortable contact when the user wears the urine collection apparatus 100 of the present invention.

Figure 6:
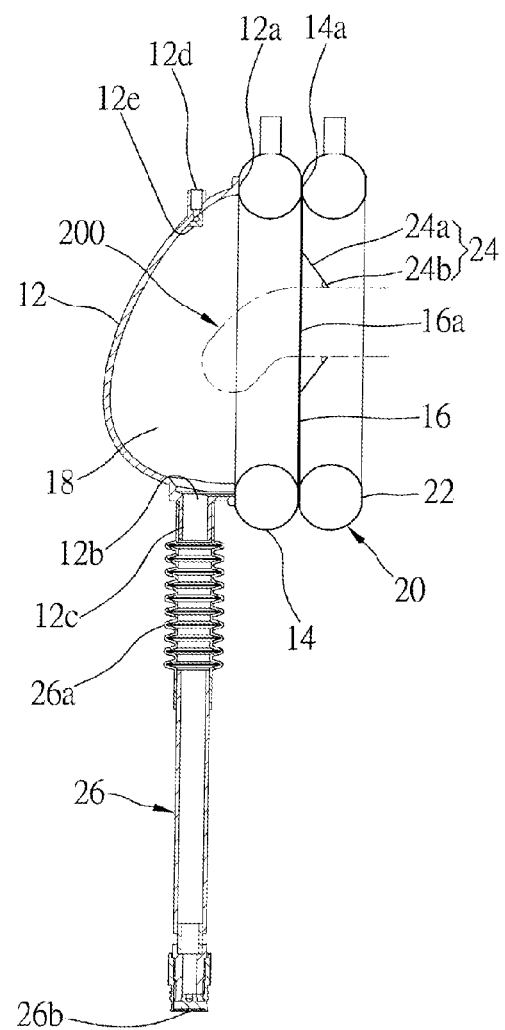
FIG. 6 is a sectional view along the 6-6 line of FIG. 4.

Furthermore, the urine cover 10 of the present embodiment has a flexible ring 24 thereon connected to the sheet 16 and surrounding the opening 16a. As shown in FIG. 6, the ring 24 has an oblique surface 24a and a stopping member 24b. The oblique surface 24a has an end connected to the sheet 16 and the other end extends outwardly and inwardly, and the distal end of the oblique surface 24a is bent inward to form the stopping member 24b. The user's penis 200 passes through the ring 24 and enters into the room 18 via the opening 16a, both of which serve good support to hold the penis 200 steadily. Meanwhile, the ring 24 has good flexibility that the urine collection apparatus 100 can be applicable for penises of different sizes. The sheet 16 and the oblique surface 24a of the ring 24 both have the function of keeping urine in the room 18 and preventing urine from backflow.

In the embodiment of the present invention, the covering member 12 of the urine cover 10 has an aperture 12b on a bottom thereof and a short connecting pipe 12c is connected to the aperture 12b to direct urine in the room 18 to a desired location such as a urine bag. The oblique surface 24a of the ring 24 can further direct urine towards the aperture 12b, and the stopping member 24b of the ring 24 can effectively hold the penis 200 and prevent urine from backflow. Moreover, in order to better control the pipe 26, in the embodiment of the present invention, the pipe 26 is further equipped with an S section 26a to help controlling the direction of a draining outlet 26b of the pipe 26.

Moreover, to better clean the urine cover 10, the urine cover 10 of the present invention has a cleaning hole 12d and a cap 12e on a top thereof. The cleaning hole 12d is communicated with the room 18 for pouring in water or washing detergent to maintain personal hygiene. The cap 12e is to close the cleaning hole 12d at an inner end thereof, and is only open during a cleaning process. The cap 12e in the present invention is a flexible cork, with an end connected to a sidewall of the covering member 12.

The description above is a usage instruction of the urine collection apparatus 100 of the preferred embodiment of the present invention. The advantages of it include collecting urine effectively, preventing urine from backflow, being easy to clean and comfortable to wear.

Figure 7:
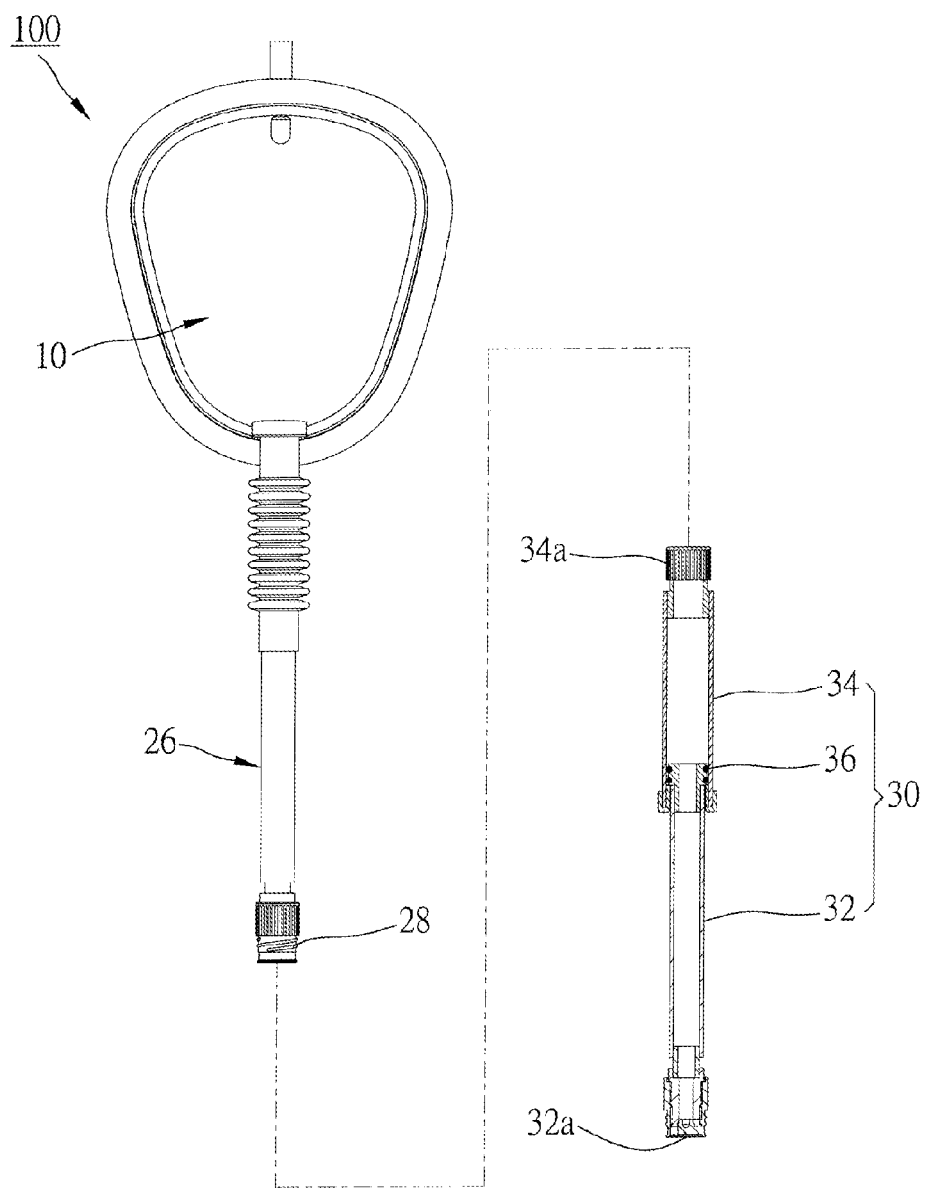
FIG. 7 is a front view of the preferred embodiment of the present invention, showing the urine collection apparatus connected to the urinating unit including the internal and external pipes.

Besides the description above, the urine collection apparatus 100 can also be applicable due to different needs. As shown in FIG. 7, the pipe 26 has a threaded connecting section 28, which is at an end opposite to the urine cover 10, to connect another urinating unit.

In the condition of changing the location of the draining outlet, a urinating unit 30 has an internal pipe 32 and an external pipe 34 fitted to the internal pipe 32 for telescoping as shown in FIG. 7. The external pipe 34 has a connecting section 34a detachably connected to the connecting section 28 of the pipe 26. The connecting section 34a applies an example of using a nut connected to one end of the external pipe 34, and the draining outlet is located at an end 32a of the internal pipe 32. The internal pipe 32 and the external pipe 34 have an anti-leaking ring 36 therebetween to prevent urine from overflow. This will not only change the location of the draining outlet, but also lengthen the applicable extent of urine direction, and accordingly, the pipe 26 and the urinating unit 30 are able to be better hidden in the pants.

Figure 8:
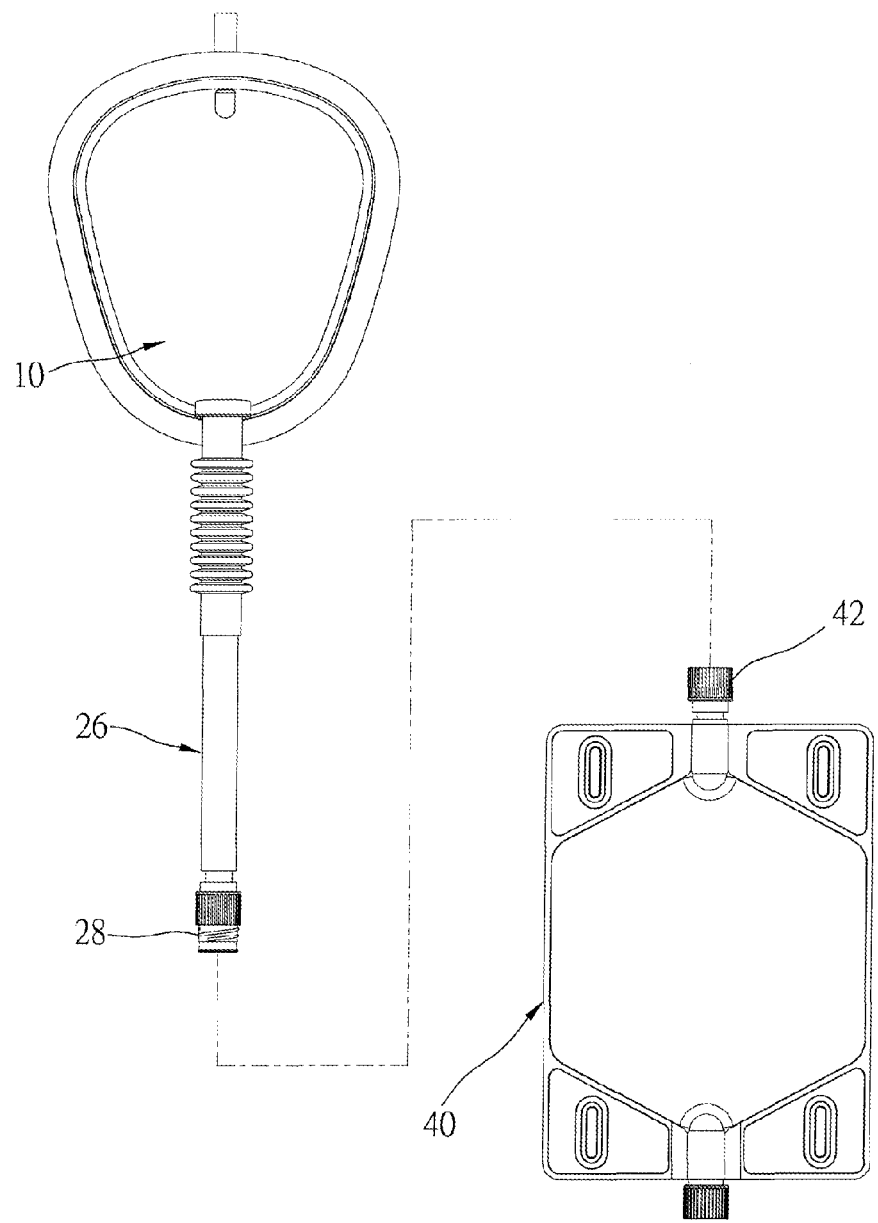
FIG. 8 is a front view of the preferred embodiment of the present invention, showing the urine collection apparatus connected to a single urine bag.

The urinating unit may also be a urine bag 40 only as show in FIG. 8, with a connecting head 42, which is a nut at an entrance of the urine bag 40, detachably connected to the threaded connecting section 28 of the pipe 26, to make the urine bag 40 connected with the pipe 26 directly.

Figure 9:
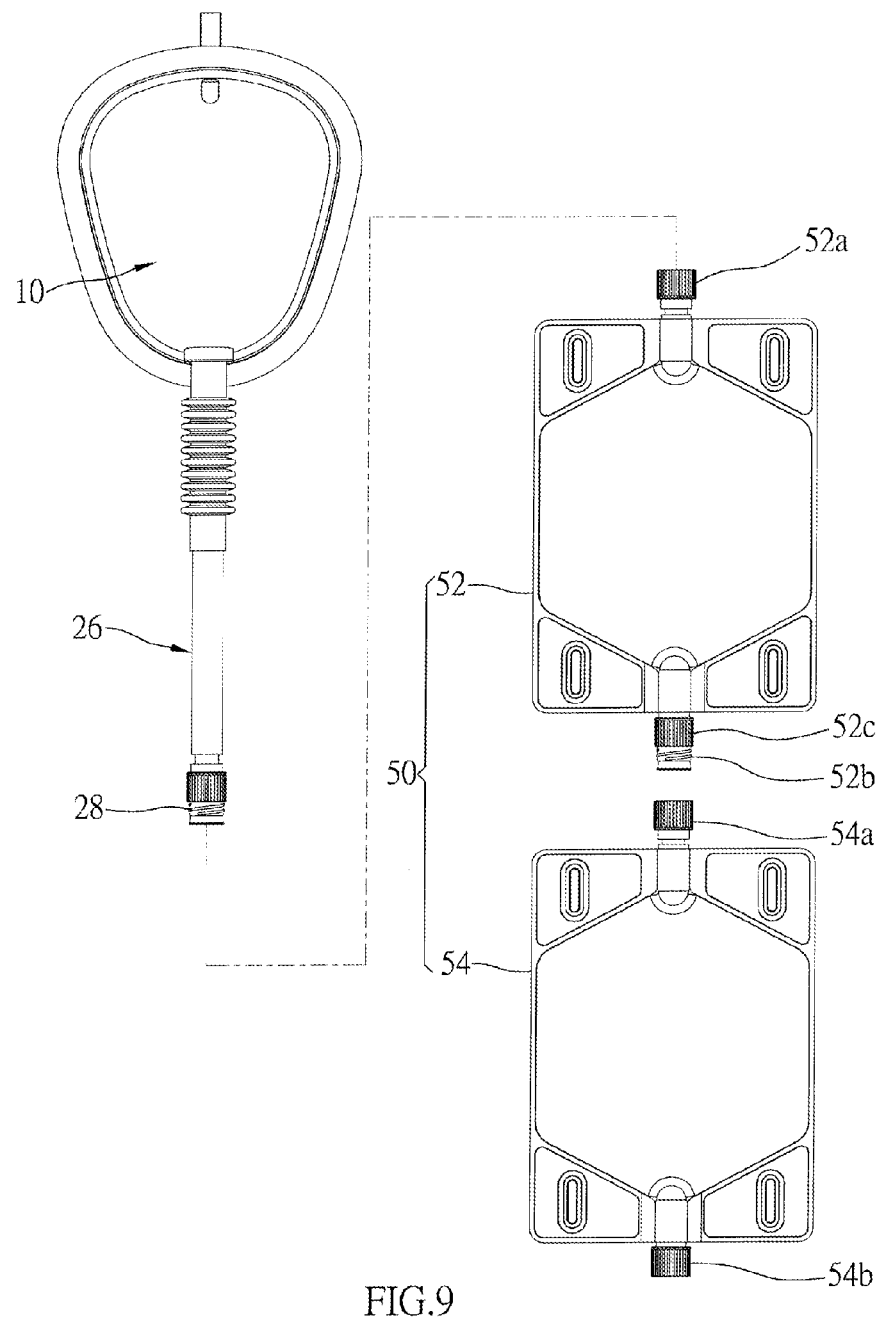
FIG. 9 is a front view of the preferred embodiment of the present invention, showing the urine collection apparatus connected to the serially connected urine bags.

FIG. 9 further shows a urinating unit 50 includes a first urine bag 52 and a second urine bag 54. The first urine bag 52 has a connecting head 52a, which is a nut, at an end thereof connected to the connecting section 28 of the pipe 26, and a threaded section 52b with a bolt 52c at the other end. The second urine bag 54, the same as the first urine bag 52, also has a connecting head 54a at an end and a bolt 54b at an opposite end. The second urine bag 54 may be serially connected to first urine bag 52 through the engagement of the connecting head 54a and the threaded section 52b. When the second urine bag 54 is full and needs to be cleaned, the user can wind up the bolt 52c which causes the first urine bag 52 disconnected to the second urine bag 54, and therefore the first urine bag 52 can still be used to collect urine, and the second urine bag 54, whose connecting head 54a is loose, can be departed from the first urine bag 52 and be cleaned.

The description above is a few preferred embodiments of the present invention. These equivalences of the present invention are still in the scope of claim construction of the present invention.

What is claimed is:

1. A urine collection apparatus for man, comprising:
a urine cover having an
annular edge,
a room therein,
an opening and
an aperture communicated with the room, whereby the room is adapted to receive a penis via the opening;
a buffer provided on the edge of the urine cover, with a surface adapted to be in touch with skin of a user; and
a pipe connected to the aperture of the urine cover;
wherein the urine cover further has a ring connected to the sheet and surrounding the opening;
wherein the urine cover further includes a flexible sheet, which is connected to the edge of the urine cover, and has the opening;
wherein the ring of the urine cover has an oblique surface with an end connected to the sheet and a distal end extending outwardly and inwardly and a stopping member on the distal end of the oblique surface;
wherein the urinating unit has an internal pipe and an external pipe, where said external pipe is fitted to the internal pipe for extension and has a connecting section to connect the connecting section of the external pipe to said internal pipe;
and
wherein an anti-leaking ring is provided between the internal pipe and the external pipe to prevent urine from overflow.

2. The urine collection apparatus as defined in claim 1, wherein the urine cover has a covering member, which has the room and an annular face, and an air bag, which has the annular edge, provided on the annular face of the covering member and connected to the buffer via the annular edge.

3. The urine collection apparatus as defined in claim 1, wherein the urine cover has a cleaning hole communicated with the room and a cap closing the cleaning hole.

4. The urine collection apparatus as defined in claim 1, wherein the buffer has an air bag.

5. The urine collection apparatus as defined in claim 1, wherein either the internal or external pipe has an end connected to the urine cover and a distal end having a connecting section to connect a urinating unit.

6. The urine collection apparatus as defined in claim 5, wherein the urinating unit is a urine bag having a connecting head connected to the connecting section of either the external pipe or internal pipe.

7. The urine collection apparatus as defined in claim 5, wherein the urinating unit has a first urine bag having a connecting head connected to the connecting section of the either the internal or the external pipe and a second urine bag detachably serially connected to the first urine bag.

8. The urine collection apparatus as defined in claim 1, where said external pipe further includes a telescoping pipe that slideably fits inside of said external pipe to further extend said external pipe.

9. The urine collection apparatus as defined in claim 3, where said cap is removable and re-attachable.

* * * * *